(12) United States Patent
Mangione et al.

(10) Patent No.: US 9,101,492 B2
(45) Date of Patent: Aug. 11, 2015

(54) SET COMPRISING AN INTERVERTEBRAL IMPLANT FOR IMMOBILISING A VERTEBRA WITH RESPECT TO ANOTHER AND AN INSTRUMENT FOR INSTALLING THIS IMPLANT

(75) Inventors: Paolo Mangione, Pessac (FR); Hervé Chataigner, Boussieres (FR)

(73) Assignee: MEDICREA INTERNATIONAL, Negron (FR)

( * ) Notice: Subject to any disclaimer, the term of this patent is extended or adjusted under 35 U.S.C. 154(b) by 868 days.

(21) Appl. No.: 13/383,030

(22) PCT Filed: Jul. 23, 2010

(86) PCT No.: PCT/IB2010/053363
§ 371 (c)(1),
(2), (4) Date: Mar. 14, 2012

(87) PCT Pub. No.: WO2011/013047
PCT Pub. Date: Feb. 3, 2011

(65) Prior Publication Data
US 2012/0165943 A1    Jun. 28, 2012

(30) Foreign Application Priority Data
Jul. 27, 2009   (FR) ..................................... 09 55238

(51) Int. Cl.
*A61F 2/46* (2006.01)
*A61F 2/44* (2006.01)
*A61F 2/30* (2006.01)

(52) U.S. Cl.
CPC ............. *A61F 2/4611* (2013.01); *A61F 2/4465* (2013.01); *A61F 2002/30378* (2013.01); *A61F 2002/30462* (2013.01); *A61F 2002/30476* (2013.01); *A61F 2002/30495* (2013.01); *A61F 2002/30538* (2013.01); *A61F 2002/30772* (2013.01); *A61F 2002/30904* (2013.01); *A61F 2002/4627* (2013.01); *A61F 2002/4629* (2013.01); *A61F 2220/0025* (2013.01); *A61F2220/0033* (2013.01); *A61F 2220/0075* (2013.01); *A61F 2250/0006* (2013.01)

(58) Field of Classification Search
CPC combination set(s) only.
See application file for complete search history.

(56) References Cited

U.S. PATENT DOCUMENTS

2006/0235426 A1    10/2006    Lim et al.

FOREIGN PATENT DOCUMENTS

| | | |
|---|---|---|
| EP | 1925271 | 5/2008 |
| FR | 2923158 | 5/2009 |
| WO | WO2008019393 | 2/2008 |

*Primary Examiner* — Christian Sevilla
(74) *Attorney, Agent, or Firm* — Defillo & Associates, Inc; Evelyn A. Defillo (57) ABSTRACT

This set comprises an intervertebral implant (2) for immobilising a vertebra (100) with respect to another and an instrument (3) for installing this implant; the implant (2) comprises a longitudinal end designed to be connected to the instrument (3), and the instrument (3) comprises a rod (26) having a free distal end (28), wherein the implant (2) is designed to be removably mounted. According to the invention: —said free distal end (28) of the instrument rod (26) is rounded; —the instrument (3) comprises releasable means (22) adapted, in a position, to retain the flexible strands (6a, 6b) in strain on each side of said rod (26), according to equivalent strains, and, in another position, to fully free these strands (6a, 6b); and—the means for mounting the implant (2) on said distal end (28) are constituted by the two flexible strands (6a, 6b) held in strain by said releasable means (22), this retaining in strain allowing to achieve mounting of the implant (2) on this distal end (28), while retaining this distal end (28) engaged in a cavity (15) of the implant (2).

15 Claims, 6 Drawing Sheets

SET COMPRISING AN INTERVERTEBRAL IMPLANT FOR IMMOBILISING A VERTEBRA WITH RESPECT TO ANOTHER AND AN INSTRUMENT FOR INSTALLING THIS IMPLANT

CROSS REFERENCE TO RELATED APPLICATION

This application is a national stage entry of PCT/IB2010/053363 filed Jul. 23, 2010, under the International Convention, claiming priority over FR 0955238 filed Jul. 27, 2009.

BACKGROUND OF THE INVENTION

This invention relates to a set comprising an intervertebral implant for immobilising a vertebra with respect to another and an instrument for installing this implant.

The invention also relates to a surgical method for immobilising a vertebra with respect to another.

It is well known to immobilise two vertebrae one with respect to another by means of an intervertebral implant in a rigid material, forming a cage defining a housing, this housing being designed to receive one or more bone grafts and/or cancellous bone chips. In some cases, the bone grafts and/or the cancellous bone chips can also be placed about the implant. The implant can restore a proper separation of the vertebrae and prevent a crash of a chip or more than one chip thereof. The immobilisation of the vertebrae with respect to the implant is achieved by the growth of bone cells on the one hand through the graft or grafts and/or chips, but also on each side of the implant, leading to what is termed a "merger" of the two vertebrae.

Some intervertebral implants have a reduced width, allowing their positioning through a posterior approach, on each side of the spinal cord. It is then generally necessary to position two implants, one on the left side of the spinal cord and the other on the right side.

This technique has the drawbacks of being relatively risky to implement, involving achieving a bone resection of the vertebra near the spinal cord, and forcing the use of reduced width implants, allowing only a small area of contact of the grafts with the vertebrae.

To overcome these drawbacks, it is possible to position an intervertebral implant by anterior approach. The approach being wider than the posterior approach, such an implant can have such a shape that it extends over a major portion of the surface of a vertebral plateau, and can therefore contain one or more grafts with a significant contact surface with the vertebral plateaus, which is a prerequisite for successful spinal fusion. An initiation through an anterior approach, however, has the disadvantage of revealing certain anatomical structures (in particular veins and arteries) that the orthopaedic surgeon or neurosurgeon is not accustomed to mobilise. This approach will therefore not be possible for a spine surgeon unless he is assisted by a colleague whose specialty is, for example, vascular surgery.

An alternative that allows solving temporarily the drawbacks of the two previous techniques consists in placing a single intervertebral implant positioned on the front side of the vertebra, occupying only a marginal surface of the intervertebral space and thereby freeing a significant surface area for the positioning of one or more grafts and/or bone chips. The implant is positioned by the posterior, side or intermediate approach between side and posterior, therefore slightly invasive. Document FR 2 923 158 describes an instrument for the introduction and implementation of such an implant, comprising a rod whose distal end is provided with means for mounting the implant, this instrument allowing (i) retaining the implant in the extension of the rod to achieve the introduction of the implant into the intervertebral space, with possible impaction, (ii) operating, once the introduction is achieved, a side pivoting of the implant with respect to the rod, in order to place the implant in the anterior position of the intervertebral space, and (iii) releasing the implant once the latter is in the position thereof of positioning in order to allow the removal of the instrument. Said mounting means comprise an articulated head equipped with a threaded rod and the implant comprises a threaded boring channel for screwing this implant on this articulated head.

Document WO 2008/019393 describes a similar instrument, connected to the implant by a double jaw, which in addition comprises a cable allowing to direct the implant with respect to the instrument.

The known instruments do not satisfy fully. In fact, the release of the implant can be difficult and achieve and lead to a change of the position of the implant during withdrawal of the instrument. The side pivoting of the implant with respect to the rod can be difficult to achieve or to control accurately, which can lead to a non optimal positioning of the implant in the intervertebral space. There is also a risk of longitudinal pivoting of the implant about itself during the operation of introducing this implant, leading to a faulty positioning of the implant; this faulty positioning is difficult to overcome once the implant is pivoted laterally or released.

OBJECTS OF THE INVENTION

The purpose of this invention is to remedy these drawbacks as a whole.

The main purpose thereof is therefore to provide a set that allows easy release of the implant, without substantial change of the position of the implant during withdrawal of the instrument.

Another purpose of the invention is to provide a set that allows achieving easy side pivoting of the implant with respect to the instrument and to control accurately this pivoting.

Still another purpose of the invention is to provide a set eliminating or significantly reducing the risk of longitudinal pivoting of the implant itself in the operation of introduction of this implant.

An additional purpose of the invention is to provide a set that allows correcting easily the position of the implant if this position proves to be faulty.

SUMMARY OF THE INVENTION

The involved set comprises, in a manner known thereto by document FR 2 923 158, an intervertebral implant allowing to immobilise a vertebra with respect to another, and an instrument for installing this implant; the implant comprises a longitudinal end designed to be connected to the instrument, having a cavity, and is connected to two flexible strands each extending from one of the longitudinal ends thereof; the instrument comprises a rod having a free distal end, on which the implant is designed to be removably mounted, this free distal end being designed to be engaged in said cavity of the implant, with possibility of pivoting of the implant with respect to the instrument; the set also comprises means for mounting the implant on said free distal end of the instrument.

According to the invention,
said free distal end of the instrument rod is rounded;
the instrument comprises releasable means, adapted, in a position, to retain the flexible strands in strain on each side of said rod, according to equivalent strains, and, in another position, to fully free these strands; and
the means for mounting the implant on said distal end of the instrument are constituted by the two flexible strands held in strain by said releasable means, this retaining in strain allowing to achieve mounting of the implant on this distal end, while retaining this distal end engaged in said cavity of the implant; releasing of the strain of the strands makes it possible to exercise a traction on either one of these strands to allow a side pivoting of the implant with respect to the distal end of the rod; the full release of the strands allows releasing the implant with respect to the instrument.

Retention of the strands on each side of the rod, as equivalent strains, thus allows positioning the implant on the distal end of the rod, in the extension of this rod, and therefore make it possible introducing the implant into the intervertebral space by using the instrument. During this introduction, the strands extend along the rod and do not hinder this introduction of the implant; once the implant inserted, the retaining means for straining the strands are released, making possible the exercise of a traction on either one of these strands in order to allow achieving a precise and controlled side pivoting of the implant about the distal end of the rod, the rounded shapes of this distal end of the cavity and the implant allowing to guide this side pivoting; once this pivoting achieved, the instrument is easily separated from the implant and can be therefore be withdrawn without risk of substantial change in the position of the implant.

The strands can also be used to withdraw the implant outside of the intervertebral space in the case where this implant would not be in the desired position.

The strands can also be used advantageously to guide one or more grafts and/or cancellous bone chips into the intervertebral space and to surround this or these grafts and/or chips, inasmuch being connected to each other, for example by knotting, so as to ensure retention of this or these grafts and/or chips among the vertebrae.

Preferably, the implant and the instrument comprise connecting means adapted to immobilize the implant with respect to the instrument about the longitudinal axis of said rod of the instrument, these connecting means being engaged when the implant is mounted on said rod in the longitudinal extension thereof.

These connecting means can thus eliminate the risk of longitudinal pivoting of the implant about itself during operation of introducing of this implant.

Preferably, said connecting means are arranged in the shape of a groove or a rib arranged at the cavity of the implant, extending in the plane of side pivoting of the implant with respect to said rod, and in the shape of a rib or a groove arranged at the distal end of the rod of the instrument, also extending in the pivoting plane of the implant with respect to said rod, the rib being designed to be engaged in the groove with the possibility of sliding.

To ensure perfect immobilisation of the implant in the extension of said rod of the instrument during operation of introducing the implant, the implant and this rod may comprise two respective holes aligning when the implant is in the introduction position with respect to said rod, the instrument further comprising a pin adapted, in this introduction position, to be engaged removably in these respective holes of the instrument and of the implant.

According to an embodiment of the invention, in this case, the hole of the implant outlets into said cavity, and the rod of the instrument is tubular and the hole that it comprises outlets axially into the distal end thereof.

The pin is thus engaged in the rod and does not hinder the introduction of the implant.

Advantageously, the hole of the implant or the hole of said rod is tapped and the distal end of the pin is threaded, this pin being in a position to be screwed into one or the other of those holes.

Retention of the implant in the introduction position is thus perfectly ensured by this screwing.

Preferably, said rod of the instrument comprises at least one pass-through guiding a flexible strand connected to the implant.

This or these pass through allow to retain the strands along the rod of the instrument.

Advantageously, in this case, this rod comprises a pass-through on the side wherein the implant is designed to be pivoted laterally, and located slightly behind the distal end of this rod, that is to say at a distance in the order of one to two centimetres from this end.

This pass-through allows retaining against the rod the strand located on the side thereto, in such a manner as not to interfere with the anatomical elements upon exerting thereto traction to achieve side pivoting of the implant.

According to a possible embodiment of the invention, said releasable means comprise at least one element mounted pivotally on the instrument, movable between a retain strain position, wherein it is folded back against the instrument and tightens a strand between the latter and the instrument, and a strain releasing position, wherein it is kept away from the instrument and allows sliding of the strand between the latter and the instrument.

Advantageously, in this case, said element comprises a lumen crossing it through, extending between a central area of this element and an end area of this element; a pin of the instrument, forming the pivot axis of this element, is engaged in said lumen with the possibility of pivoting and of sliding therein; said element is thus capable of being slid with respect to the instrument in such a way that the pin forming the axis is placed at the end of the lumen located towards the central area of the element, thereby immobilising this element to pivot with respect to the instrument; this same element is also capable to be slid with respect to the instrument in such a manner that said pin forming the axis is placed at the end of the lumen located towards the end area of the element, thereby allowing the pivoting of this element with respect to the instrument and corresponds to said strain releasing position.

An easy actuation of the instrument is thus obtained along with a simple structure and easy to sterilise.

According to another possible embodiment of the invention, the instrument comprises a ring axially mobile mounted thereon, moving between a first axial position for retaining strain, wherein the ring tightens a strand or the two strands between itself and the instrument, and a second axial position, for releasing strain, wherein the ring allows sliding of the strand or strands between itself and the instrument. In particular, this ring can be screwed and unscrewed on a grip handle that comprises the instrument, this screwing/unscrewing allowing the latter passing-through said first axial position to said second axial position and vice versa.

The invention also relates to a surgical method for immobilizing a vertebra with respect to another, comprising the steps consisting of:

using the set as specified above;

engaging the implant on the distal end of the instrument rod and then actuate said releasable means so as to place the strands in strain and retain these strands in strain, in order to achieve setting of the implant on the distal end of the instrument rod;

inserting the implant between the vertebral plateaus of two vertebrae by means of said instrument, part of these strands exceeding outside the patient;

actuating said releasable means so as to release at least partially the strain of these strands;

achieving a side pivoting of the implant with respect to the distal end of said rod by using a strand or the two strands for directing and positioning the implant in the intervertebral space or to correct the position of the implant in the Intervertebral space;

fully unlocking the strands of the instrument to leave the implant in place in the intervertebral space, and withdraw the instrument.

The method may comprise the step consisting of withdrawing the implant outside the intervertebral space in the case where the implant would not be in the desired position, by traction on the strands.

The method may also comprise the steps consisting of:

introducing one or more grafts and/or cancellous bone chips between the strands, in the intervertebral space; and using the strands in such a manner as to retain this graft, or these grafts, and/or chips between the vertebrae and compact them.

The invention will be better understood, and other characteristics and advantages thereof will become evident, with reference to the annexed schematic drawing, representing, by way of non exhaustive examples, one embodiment of the intervertebral implant that it relates, and two embodiments of the instrument that it relates.

DESCRIPTION OF THE PREFERRED EMBODIMENTS

Figure 9:
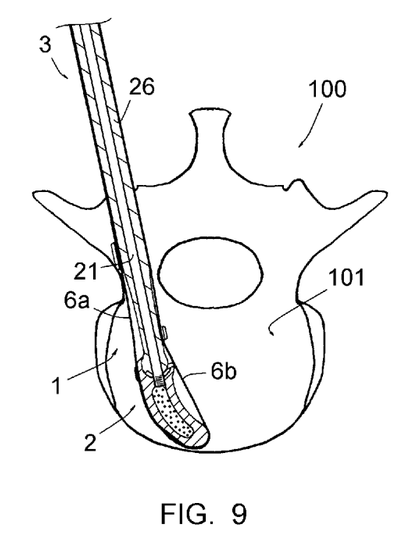
FIGS. 9 to 11 are top views of the implant and of the instrument during different successive steps of positioning of the implant between the plateaus of the two vertebrae.
Figure 10:
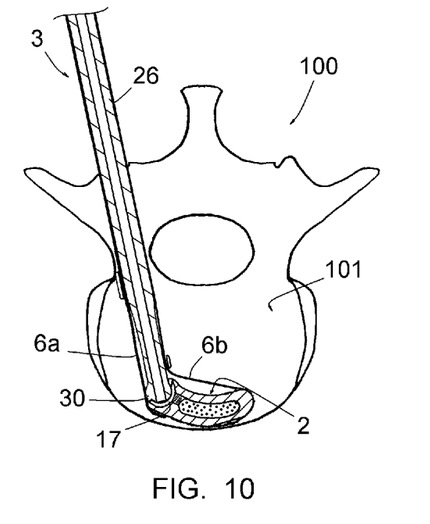
Figure 11:
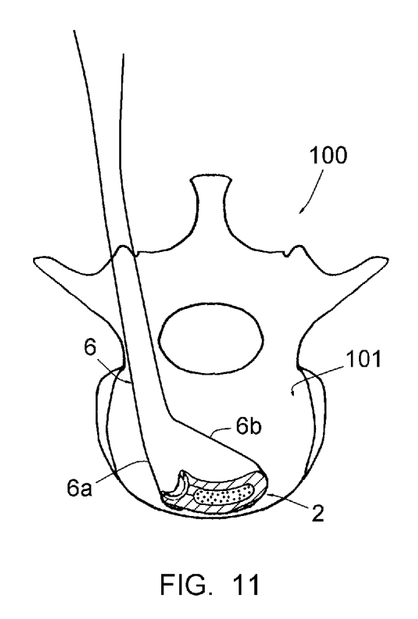

FIGS. 9 to 11 represent a set 1 comprising an intervertebral implant 2 allowing immobilising a vertebra 100 with respect to the overlying vertebra 100 and an instrument 3 of positioning this implant 2 between the plateaus 101 of the two vertebrae.

Figure 1:
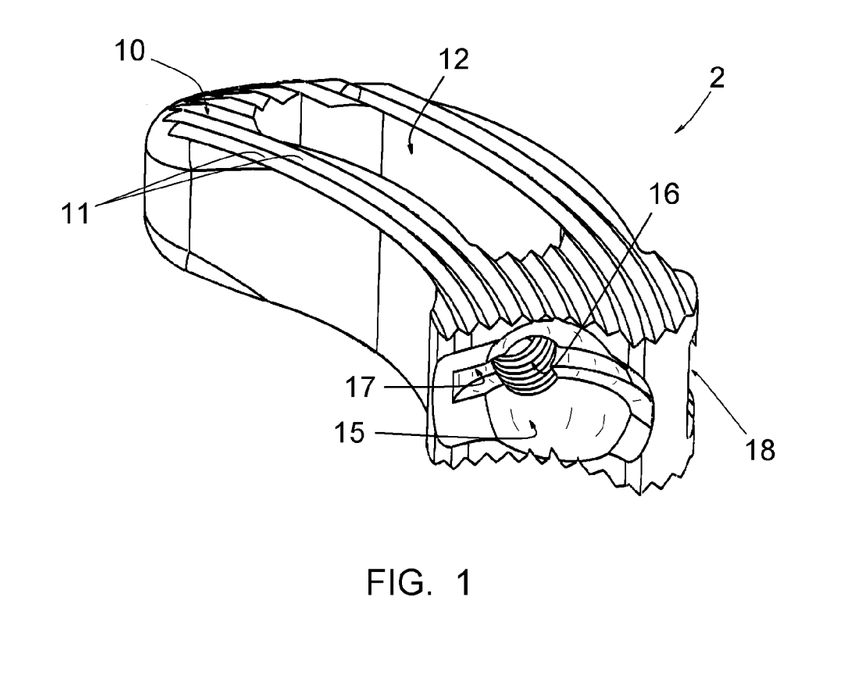
FIG. 1 is a perspective view of the implant.
Figure 2:
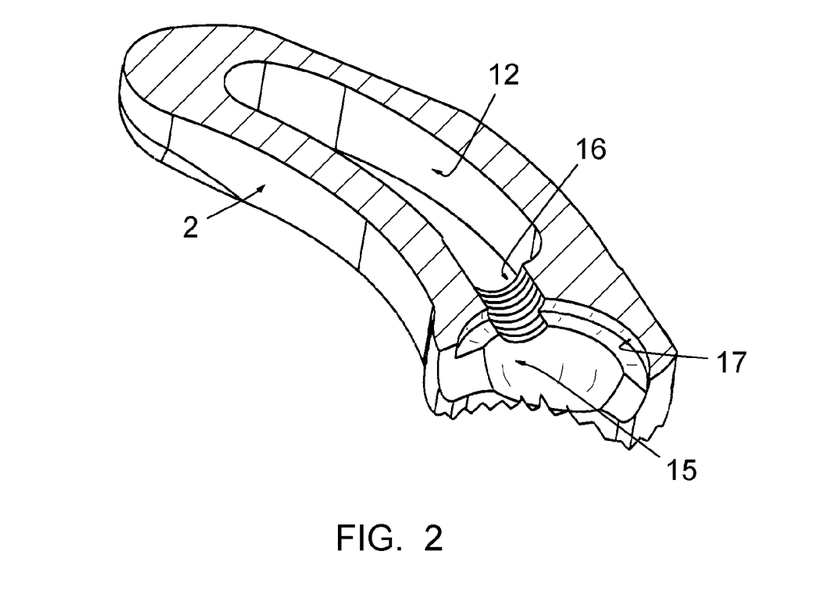
FIG. 2 is a view similar to FIG. 1 with central longitudinal cross-section in the direction of the thickness thereof.
Figure 3:
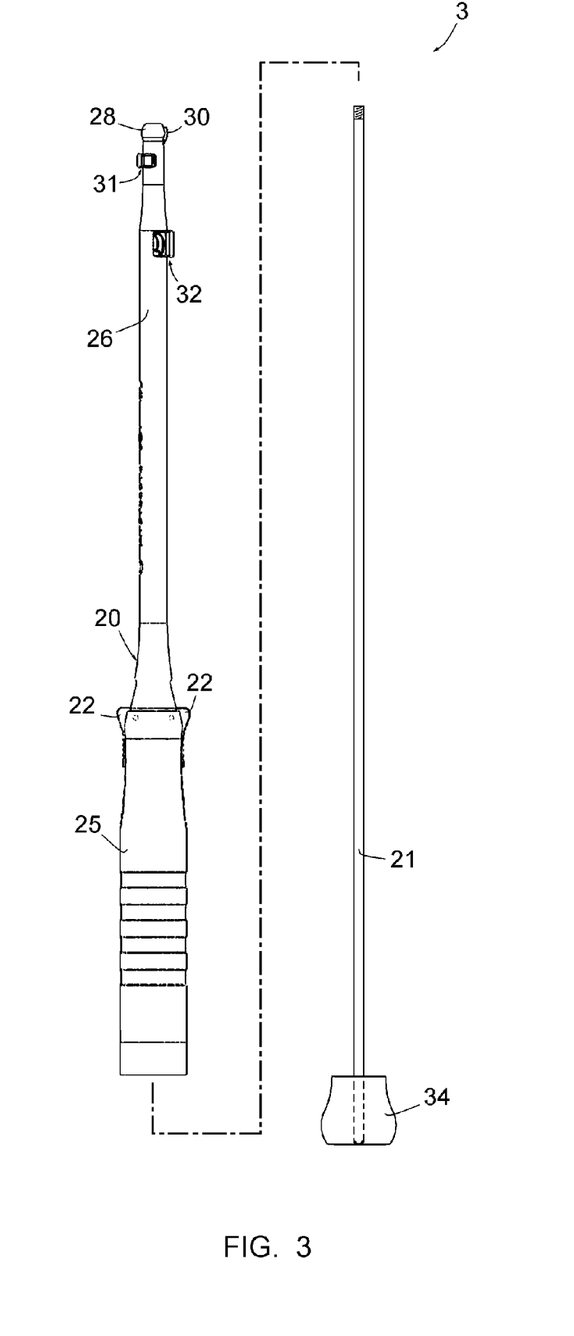
FIG. 3 is a top view of the instrument, in a disassembled state, according to a first embodiment.

As shown more particularly in FIGS. 1 and 2, the implant 2 is designed to be inserted between the plateaus 101 of the two vertebrae 100 to be immobilised and is connected to a flexible link or ligament 6 forming two strands 6a, 6b exceeding from this implant.

The implant 2 has a curved shape substantially corresponding to the curvature shown by the anterior surface of the element of a vertebra 100 and such length that it occupies, once positioned in place, between the plateaus 101, a portion of the area of these plateaus along this anterior approach (see FIGS. 9 to 11). Moreover, it has such a width that it can be introduced into the intervertebral space to be treated by posterior approach, as shown, by side approach or intermediate approach between the posterior approach and the side approach.

As shown more particularly in FIG. 1, the implant 2 has faces 10 designed to come into contact with the plateaus 101, equipped with series of triangular cross-section ribs 11. These ribs 11 provide support grip without slipping of the implant 2 against the plateaus 101.

The implant 2 also comprises an inner housing 12 discharging in the faces 10. This housing 12 is designed to receive one or more grafts and/or cancellous bone chips before its introduction into the intervertebral space.

It also comprises a hemispherical-shaped cavity 15, arranged in the longitudinal end thereof designed to be connected to the instrument 3, a threaded boring channel 16 discharging into the bottom of the cavity 15, substantially coaxially thereto, and a curved groove 17. As can be seen in FIGS. 1 and 2, this groove 17 extends perpendicular to the thickness of the implant 2, substantially halfway up thereto, from the anterior side edge of the cavity 15 up to beyond the boring channel 16, and the curvature thereof is cantered on the centre of the cavity 15.

Figures 5, 5A, 5B, 6:
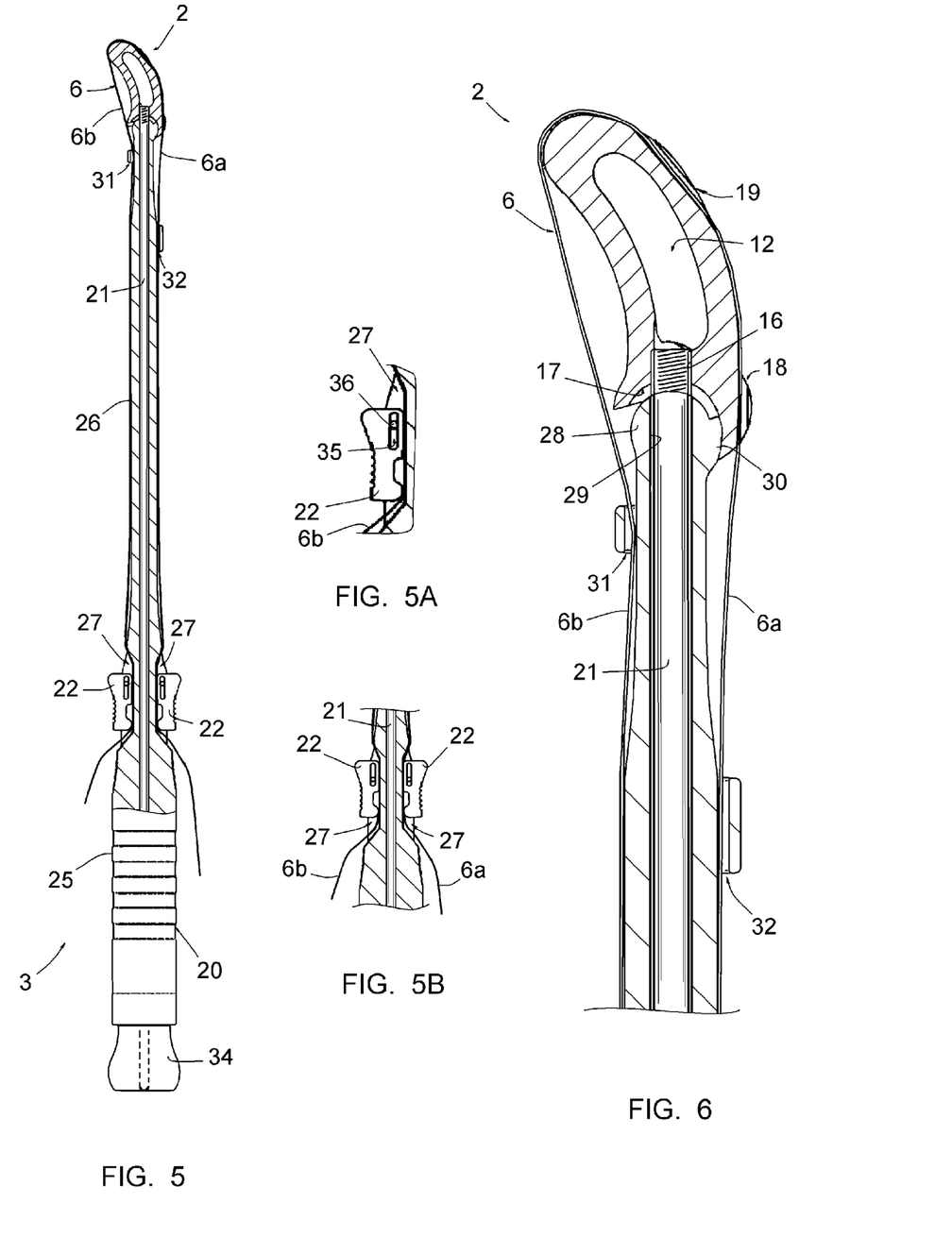
FIG. 5 is a view of the instrument and the implant similar to FIG. 4, except that said strands are in strain and that said retaining elements in strain are in a folded back position against the grip handle of the instrument but are not immobilised with respect to this grip handle.
FIG. 5A is a partial view of the instrument similar to FIG. 5, on an enlarged scale.
FIG. 5B is a partial view of the instrument similar to FIG. 5, with said retaining elements in strain in immobilisation position with respect to the grip handle of the instrument.
FIG. 6 is a view of the implant and of the distal part of the instrument rod, similar to FIG. 5, on an enlarged scale.
Figure 7:
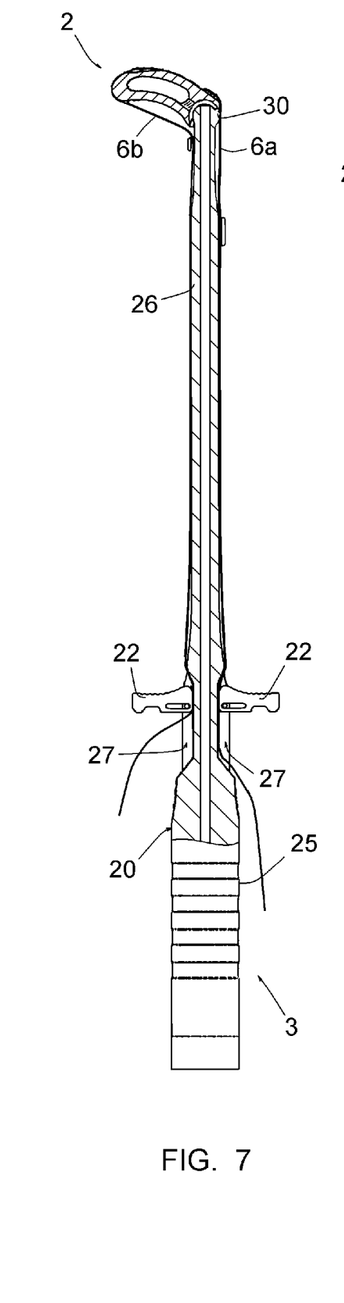
FIG. 7 is a view of the instrument and of the implant similar to FIG. 4, but with the implant placed in a side pivoting position with respect to the rod of the instrument, and the retaining elements in strain a releasing position of the strain of the strands.
Figure 8:
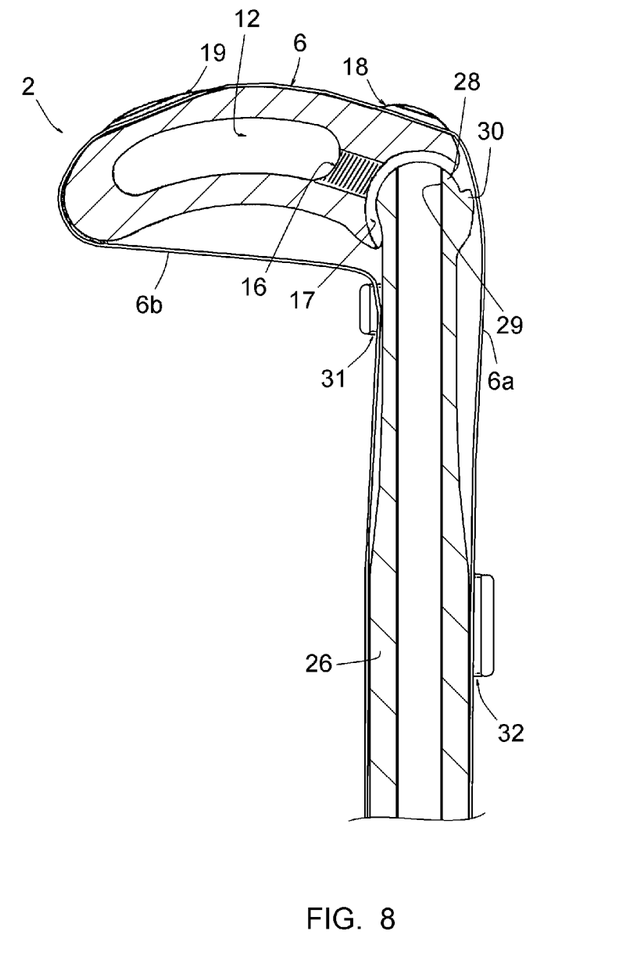
FIG. 8 is a view of the implant and of the distal part of the rod of the instrument, similar to FIG. 7, on an enlarged scale, the implant being in a position of full side pivoting with respect to the rod instrument.

Moreover, the implant 2 comprises two internal conduits 18, 19 arranged at its convex surface, enabling the sliding engagement of the ligament 6, one of these conduits 18 being located at said longitudinal end of the implant 2 designed to be connection to the instrument 3, and the other conduit 19 being located at the side of the other end of the implant 2. The ligament 6 thus extends along the convex surface of the implant 2 and forms the strand 6a at the longitudinal end of the implant 2 designed to be connection to the instrument 3, and the strand 6b at the opposite end, as can be seen in FIG. 6 or 8.

In particular, the ligament 6 can be formed by a braided implantable fibrous material, for example polyester. It is preferably flattened and has a width substantially corresponding to the height of the intervertebral space to be restored, or slightly lower with respect to this height.

With reference to FIGS. 3 to 6, it is evident that the instrument 3 comprises a body 20, a pin 21 and two releasable elements 22 for retaining the strands 6a, 6b under strain.

The element 20 is tubular. It comprises a gripping grip handle 25 and a rigid rod 26.

The grip handle 25 forms two diametrically opposite grooves 27, extending in the plane of the side pivoting of the implant 2 with respect to the instrument 3 (which is the plane of the cross-sections shown in FIGS. 4 to 8) and at which level the elements 22 are mounted in a pivoting manner.

The rod 26 comprises a rounded distal end 28, substantially spherical, perforated axially by a boring channel 29 and comprising a curved projecting rib 30 extending laterally in the said plane, as shown in FIG. 6 or 8. The distal end 28 is designed to be engaged in the cavity 15 and the rib 30 is designed to be received in the groove 17 with possibility of sliding. The hole 16 is opposite the boring channel 29 in said introduction position for the implant 2 shown in FIGS. 5 and 6.

The rod 26 also comprises two pass through 31, 32 on two diametrically opposite sides, also located in said plane. One of these pass through 31 is placed on the side onto which the implant 2 is designed to be pivoted laterally, slightly backward from the distal end 28, that is to say at a distance in the order of one to two centimetres from this end; the other pass-through 32 is positioned further backward from this end 28.

The pin 21 is threaded at one end and comprises a gripping head 34 at the other end thereof. It is designed to be engaged in the body 20 by the threaded end thereof, up to the through-pass of the boring channel 29 and to be screwed into the threaded hole 16 of the implant 2. In the position of full screwing shown in FIGS. 4 to 6, the head 34 abuts against the grip handle 25 of the body 20, ensuring the immobilisation of the implant 2 with respect to the instrument 3 in said introduction position.

As shown in greater detail in FIG. 5A, each releasable element 22 comprises a detachable lumen 35 crossing it from side to side, extending between a central area of this element 22 and an end area of this element; a pin 36 of the Instrument 3, forming the pivoting axis of this element 22, is engaged in the lumen 35 with the possibility of pivoting and sliding therein, said element 22 is thus capable to be slid with respect to the instrument in such a manner so that pin 36 be placed at the end of the lumen 35 located towards the central area of the element 22, thereby immobilising this element 22 pivoting with respect to the instrument 3 (see FIG. 5B); this very element 22 is also capable to be slid with respect to the instrument 3 in such a manner that the pin 36 is placed at the end of the lumen 35 located toward the end area of the element 22, thereby allowing pivoting of this element with respect to the instrument 3 (see FIGS. 5 and 5a).

Figure 4:
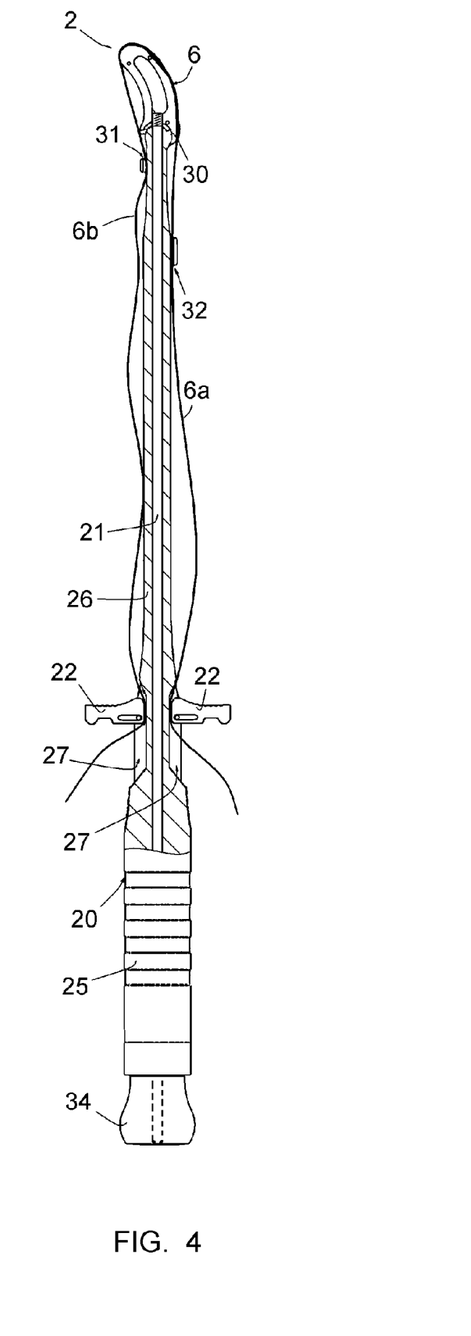
FIG. 4 is a view of the instrument similar to FIG. 3, in the mounted state and partly in cross-section, with the mounting of the implant on the distal end of a rod that comprises this instrument; the implant is placed in a introduction position into an intervertebral space, and retaining elements in strain of flexible strands connected to this implant are in a position of releasing the strain of these strands.

Each element 22 is thus movable between a retaining position of the strain shown in FIG. 5 (unlocked position) or 5B (locked position), wherein it is folded back against the instrument and tightens a strand 6a, 6b between itself and the grip handle 25, and a releasing position the strain shown in FIG. 4, wherein it is kept away from the grip handle 25 and allows sliding of the strand 6a, 6b between itself and the grip handle 25.

To facilitate the handling thereof, each element 22 comprises an eminence above the lumen 35, forming a support for a thumb of the user, and a ribbed anti-slip surface, outside from this eminence.

In practice, as shown in FIG. 9, the housing 12 is lined with one or more grafts and/or chips of bone and the implant 2, in the setting phase shown in FIGS. 5 and 6, under strain of the strands 6a, 6b, is introduced into the intervertebral space by using the instrument 3, by posterior, side or intermediate approach, with possible impaction.

During this introduction, the rib 30 is engaged in the groove 17, thereby preventing any risk of longitudinal pivoting of the implant 2 with respect to the instrument 3, which could lead to faulty positioning of this implant 2.

Once the latter is introduced, the pin 21 is unscrewed and the strain of the strands 6a, 6b is slightly released by manoeuvring the elements 22, to allow side pivoting of the implant 2 with respect to the instrument 3, as shown FIG. 10.

The strain of the strands 6a, 6b is then released, making possible the exercise of strain in one or the other of these strands to allow a precise and controlled side pivoting of the implant 2 with respect to the distal end 28 of the rod 26.

Once the implant 2 is in place on the anterior side of the end plateaus 101 (FIG. 10), the strands 6a, 6b are released from the instrument 3 and the latter is withdrawn (FIG. 11).

In the case where the implant 2 would not be in the desired position, the strands 6a, 6b can be used to remove the implant 2 out of the intervertebral space and repeat the operations of introduction and positioning.

These strands 6a, 6b can be used advantageously to guide one or more grafts and/or cancellous bone chips into the intervertebral space and to surround this, or these, grafts and/or chips, by being connected to one another, for example by knotting, in order to ensure retaining of this, or these, grafts and/or chips between the vertebrae.

Figure 12:
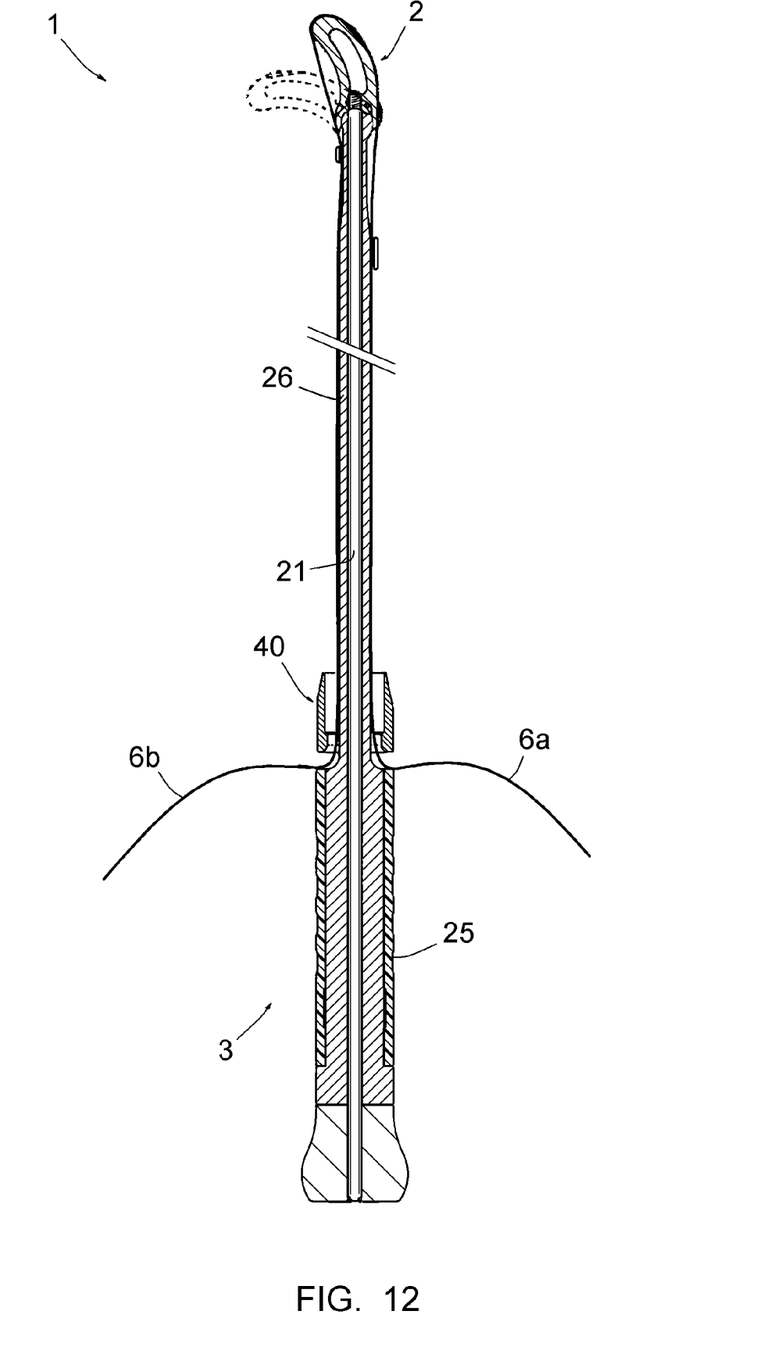
FIG. 12 is a cross-section top view of the instrument, according to a second embodiment.

FIG. 12 shows a set 1 identical to that described above, except that in this set, the elements 22 are replaced by a ring 40 axially movable on a conical area of the instrument 3, this ring 40 being movable between a first axial position, of retaining the strain of the strands 6a, 6b, wherein the ring tightens the two strands between itself and the instrument 3, and a second axial position, of releasing the strain, wherein it allows sliding of the strands 6a, 6b between itself and the instrument 3.

It is evident from the foregoing that the invention provides a set 1 showing the key advantages of (i) allowing an easy release of the implant 2, without substantial change in the position of this implant during withdrawal of the instrument 3, (ii) achieving easily the side pivoting of the implant 2 with respect to the instrument 3 and controlling precisely this pivoting, (iii) eliminating or greatly reducing the risk of longitudinal pivoting of the implant 2 thereon during the introduction operation of this implant, and (iv) allowing to correct easy the position of the implant 2 if this position proved to be defective.

The invention has been described above with reference to embodiments given solely by way of an example. It is understood that it is not limited to these embodiments but that it extends to all other embodiments covered by the hereby annexed claims.

The invention claimed is:

1. A set comprising:
   an intervertebral implant for immobilizing a vertebra with respect to another; and
   an instrument for installing the implant;
   the implant comprises a longitudinal end designed to be connected to the instrument, the longitudinal end including a cavity, the longitudinal end is connected to two flexible strands, each flexible strand extending from the longitudinal end of the implant;

the instrument comprises a rod having a free distal end, on which the implant is designed to be removably mounted, the free distal end being designed to be engaged in said cavity of the implant, with possibility of pivoting of the implant with respect to the instrument;

the set also comprises a mounting device for mounting the implant on said free distal end of the rod;

wherein:

said free distal end of the rod is rounded;

the instrument comprises a releasable device adapted, in a first position, to retain the flexible strands in strain on each side of said rod, according to equivalent strains, and, in a second position, to fully free these strands; and the mounting device is constituted by the two flexible strands held in strain by said releasable device, this retaining in strain allowing to achieve mounting of the implant on the distal end, while retaining the distal end engaged in said cavity of the implant; releasing of the strain of the strands makes it possible to exercise a traction on either one of the strands to allow a side pivoting of the implant with respect to the distal end of the rod; the full release of the strands allows releasing the implant with respect to the instrument.

2. The set according to claim 1, wherein the implant and the instrument comprise at least one connecting device adapted to immobilize the implant with respect to the instrument about the longitudinal axis of said rod of the instrument, the at least one connecting device being engaged when the implant is mounted on said rod in the longitudinal extension.

3. The set according to claim 2, wherein said at least one connecting device is arranged in the shape of a groove or a rib arranged at the cavity of the implant, extending in a plane of side pivoting of the implant with respect to said rod, and in the shape of a rib or a groove arranged at the distal end of the rod of the instrument.

4. The set according to claim 1, wherein said implant and said rod comprise two respective holes aligning when the implant is in an introduction position with respect to said rod, the instrument further comprising a pin adapted, in the introduction position, to be removably engaged in the respective holes of the instrument and of the implant.

5. The set according to claim 4, wherein the hole of the implant outlets into said cavity, and the rod of the instrument is tubular and the hole that it comprises outlets axially into the distal end of the rod.

6. The set according to claim 5, wherein the hole of the implant or the hole of said rod is tapped, and in that a distal end of the pin is threaded.

7. The set according to claim 1, wherein said rod of the instrument comprises at least one pass-through guiding a flexible strand connected to the implant.

8. The set according to claim 7, wherein said rod comprises a pass-through on the side wherein the implant is designed to be laterally pivoted, and located behind the distal end of this rod, at a distance of one to two centimeters from the end.

9. The set according to any of claim 1, wherein said releasable device comprises at least one element pivotally mounted on the instrument, movable between a retain strain position, wherein when the at least one element it is folded back against the instrument, tightens a strand between the latter and the instrument, and a strain releasing position, wherein when the at least one element is kept away from the instrument and allows sliding of the strand between the latter and the instrument.

10. The set according to claim 9, wherein said element comprises a lumen crossing through the element, extending between a central area of the element and an end area of the element; a pin of the instrument, forming the pivot axis of the element, is engaged in said lumen with the possibility of pivoting and of sliding therein; said element is slid with respect to the instrument in such a way that the pin forming the axis is placed at the end of the lumen located towards the central area of the element, thereby immobilizing the this element to pivot with respect to the instrument; the element also slides with respect to the instrument in such a manner that said pin forming the axis is placed at the end of the lumen located towards the end area of the element, thereby allowing the pivoting of this element with respect to the instrument and corresponds to said strain releasing position.

11. The set according to any of claim 1, wherein the instrument comprises a ring axially mobile mounted thereon, moving between a first axial position for retaining strain, wherein the ring tightens a strand or the two strands between itself and the instrument, and a second axial position, for releasing strain, wherein the ring allows sliding of the strand or strands between itself and the instrument.

12. The set comprising the implant according to claim 11, wherein the ring is screwed and unscrewed on a grip handle that comprises the instrument, this screwing/unscrewing allowing the latter passing-through said first axial position to said second axial position and vice versa.

13. A surgical method for immobilizing a vertebra with respect to another, comprising the steps of:

using the set as set forth in claim 1;

engaging the implant on the distal end of the instrument rod and then actuating said releasable device to place the strands in strain and retain the strands in strain, to achieve setting of the implant on the distal end of the rod of the instrument inserting the implant between the vertebral plateaus of two vertebrae by using said instrument, part of these strands exceeding outside the patient;

actuating said releasable device so as to release at least partially the strain of the strands;

achieving a side pivoting of the implant with respect to the distal end of said rod by using a strand or the two strands for directing and positioning the implant in the intervertebral space or to correct the position of the implant in the intervertebral space;

fully unlocking the strands of the instrument to leave the implant in place in the intervertebral space, and withdraw the instrument.

14. The surgical method according to claim 13, wherein further comprising the steps of withdrawing the implant outside the intervertebral space in the case where the implant would not be in the desired position, by traction on the strands.

15. The surgical method according to claim 13, further comprising the steps of:

introducing one or more grafts and/or cancellous bone chips between the strands, in the intervertebral space; and using the strands in such a manner as to retain this graft, or these grafts, and/or chips between the vertebrae and compact them.

* * * * *